(12) United States Patent
Pankhurst et al.

(10) Patent No.: US 8,074,970 B2
(45) Date of Patent: Dec. 13, 2011

(54) DISPERSING FRAGRANCES

(75) Inventors: Richard P. H. Pankhurst, London (GB); Brian D. Smith, London (GB); Michael J. Evans, London (GB)

(73) Assignee: CTR Consultoria Técnica e Representações Lda., Samora Correia (PT)

( * ) Notice: Subject to any disclaimer, the term of this patent is extended or adjusted under 35 U.S.C. 154(b) by 0 days.

(21) Appl. No.: 12/720,126

(22) Filed: Mar. 9, 2010

(65) Prior Publication Data

US 2010/0163639 A1 Jul. 1, 2010

Related U.S. Application Data

(60) Continuation of application No. 12/028,071, filed on Feb. 8, 2008, now abandoned, which is a division of application No. 10/491,718, filed on Aug. 5, 2004, now Pat. No. 7,344,123.

(30) Foreign Application Priority Data

Oct. 4, 2001 (GB) .................................. 0123851.8

(51) Int. Cl.
*B01F 3/04* (2006.01)
(52) U.S. Cl. ........ 261/26; 261/30; 261/65; 261/DIG. 88; 422/5
(58) Field of Classification Search .................... 261/26, 261/30, 62, 65, 119.1, DIG. 65, DIG. 88; 422/5, 123
See application file for complete search history.

(56) References Cited

U.S. PATENT DOCUMENTS

| | | | | |
|---|---|---|---|---|
| 3,993,444 | A | * | 11/1976 | Brown ........................ 422/116 |
| 4,067,692 | A | * | 1/1978 | Farris ............................ 422/124 |
| 4,339,079 | A | * | 7/1982 | Sato et al. ...................... 239/43 |
| 5,023,020 | A | * | 6/1991 | Machida et al. ............. 261/18.1 |
| 5,167,877 | A | * | 12/1992 | Pai ................................ 261/18.1 |
| 5,565,148 | A | * | 10/1996 | Pendergrass, Jr. ............. 261/30 |
| 5,884,808 | A | * | 3/1999 | Muderlak et al. ............... 222/23 |
| 6,254,065 | B1 | * | 7/2001 | Ehrensperger et al. ......... 261/26 |
| 6,267,297 | B1 | * | 7/2001 | Contadini et al. ............... 239/1 |
| 6,390,453 | B1 | * | 5/2002 | Frederickson et al. ......... 261/26 |
| 6,581,915 | B2 | * | 6/2003 | Bartsch et al. .................. 261/26 |
| 6,619,559 | B2 | | 9/2003 | Wohrle |
| 6,712,287 | B1 | | 3/2004 | Le Pesant et al. |
| 6,713,024 | B1 | * | 3/2004 | Arnell et al. .................. 422/124 |
| 2003/0026728 | A1 | * | 2/2003 | Avram ............................ 422/4 |

* cited by examiner

*Primary Examiner* — Charles Bushey
(74) *Attorney, Agent, or Firm* — Stites & Harbison PLLC; Douglas E. Jackson

(57) ABSTRACT

A fragrance disperser in one form includes a single fan that passes air over a wicked single or double fragrance. A second form has the fan reversible to provide two different airstreams that evaporate respective different fragrances one after the other. Where two fragrances are provided, the evaporation may be by respective electrical heaters. A fragrance source may be formed by two sheets joined together to form two chambers each receiving a respective wick and having respective exposed wick portions. The source may incorporate a source of electrical power. An alternative source has a reservoir for fragrance and a wick located in an air passage forming part of the source so that an air flow is guided through the passage past the wick to evaporate fragrance. Where two fragrances are provided, the fragrance sources may be located side-by-side and matching fragrances may have, for example, matching indicia on the sources so that the match can be easily determined visually.

24 Claims, 15 Drawing Sheets

Electronic circuit controls the on/off times of the fragrances
T1 = time on for fragrance 1
T2 = dwell period between fragrances 1 and 2
T3 = time on for fragrance 2
T4 = dwell period between fragrance 2 and 1

Electronic circuit controls the on/off times of the fragrances
T1 = time on for fragrance 1
T2 = dwell period between fragrances 1 and 2
T3 = time on for fragrance 2
T4 = dwell period between fragrance 2 and 1

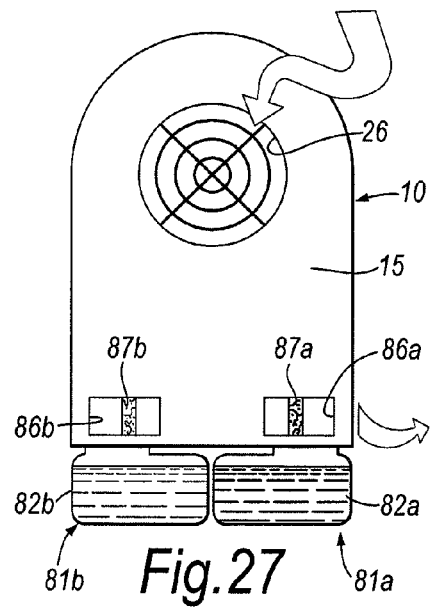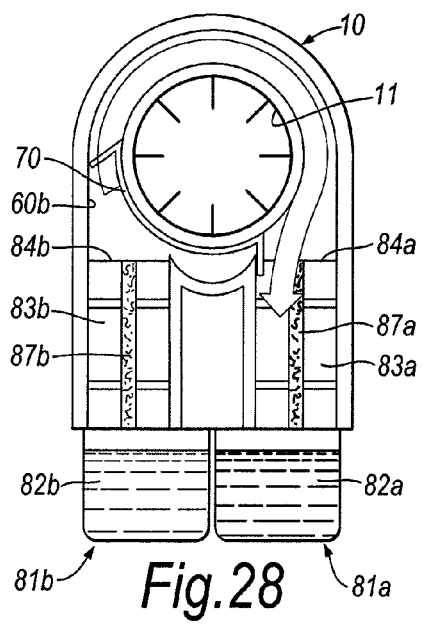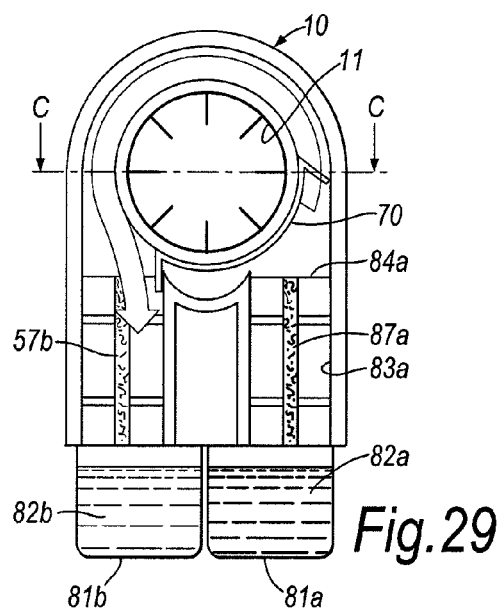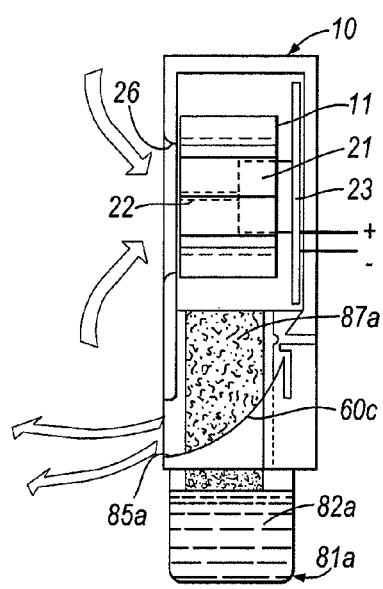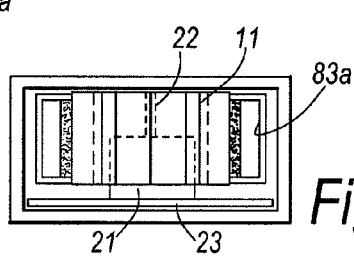

DISPERSING FRAGRANCES

CROSS REFERENCE TO RELATED APPLICATIONS

This application is a continuation of application Ser. No. 12/028,071, filed Feb. 8, 2008, now abandoned; which is a divisional of application Ser. No. 10/491,718, filed Aug. 5, 2004, now U.S. Pat. No. 7,344,123, issued: Mar. 18, 2008 (which are hereby incorporated by reference).

BACKGROUND OF THE INVENTION

The invention relates to fragrance dispersers, fragrance sources and fragrance containers.

Fragrance dispersers are used to release one or more fragrances into an enclosed space such as a room. In general, the fragrance is held by a fragrance source and released either by natural convection or by forced convection or by heating a wick or pad, for example, holding the fragrance.

BRIEF SUMMARY OF THE INVENTION

According to a first aspect of the invention, there is provided a fragrance disperser comprising a source of fragrance and means for generating a flow of air to release said fragrance.

One form of fragrance source is a container containing a liquid fragrance. The fragrance is released by a convection air current passing across an outlet for the fragrance. It is a problem that this does not provide a directed flow of air.

According to a second aspect of the invention, there is provided a fragrance container comprising a reservoir for receiving a liquid fragrance and an outlet to the reservoir, the outlet defining a path for a flow of air to release fragrance in the reservoir.

Many fragrance sources are complicated to manufacture including separate containers and wicks.

According to a third aspect of the invention, there is provided a fragrance source comprising a back sheet and a front sheet with a wicking material therebetween the back sheet and the front sheet being joined together along a closed line to define a reservoir for fragrance, a portion of the wicking material being exposable outside the closed line for releasing the fragrance, the join being such as to allow the wicking material to wick fragrance from the reservoir to the exposable portion.

According to a fourth aspect of the invention, there is provided a fragrance disperser comprising two sources of fragrance, means for dispersing fragrance from said sources and a control system for controlling said dispersing means.

BRIEF DESCRIPTION OF THE DRAWINGS

The following is a more detailed description of some embodiments of the invention, by way of example, reference being made to the accompanying drawings in which:

FIG. 27 is a front elevation of a third form of fragrance disperser and two fragrance sources, FIG. 28 is a front elevation of the third form of fragrance disperser with a front cover removed and showing a fan rotating in one sense, FIG. 29 is a similar view to FIG. 24 but showing the fan rotating in an opposite sense, FIG. 30 is a cut away side elevation of the fragrance disperser of FIGS. 28 and 29, FIG. 31 is a cross-section on the line C-C of FIG. 29.

DETAILED DESCRIPTION OF THE INVENTION

Referring first to FIGS. 1 to 4, the fragrance disperser is formed by a housing 10, a fan 11 and a fragrance source 12.

Figure 2:
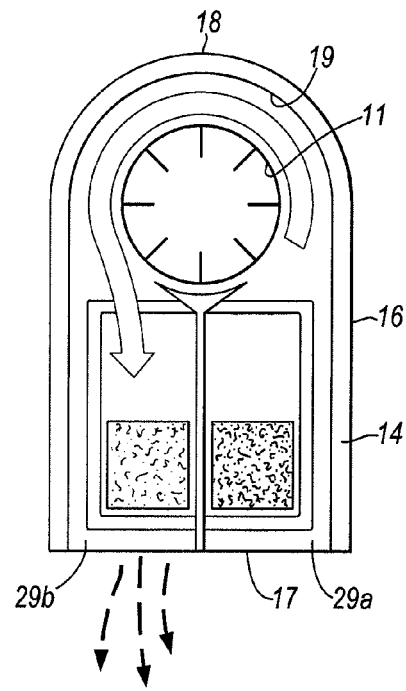
FIG. 2 is a similar view to FIG. 1 but showing the fan rotating in an opposite sense.
Figure 3:
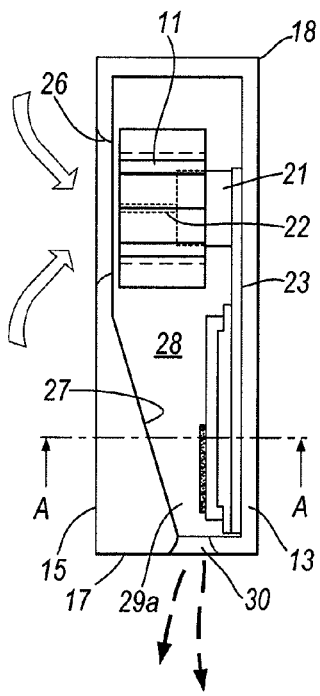
FIG. 3 is a cut-away side elevation of the fragrance disperser of FIGS. 1 and 2.

The housing 10, which may be formed of any suitable material such as metal or plastics, is formed by a back wall 13, a side wall 14 and a front cover 15 (seen in FIG. 3). The back wall 13 is generally rectangular with parallel side edges 16 interconnected at one end by a straight lower end edge 17 and at the other end by a generally semi-circular end edge 18. The side wall 14 extends around the side edges 16 and the semi-circular upper end edge 18. The portion of the side wall 14 extending around the upper end edge 18 has an interior surface 19 (see FIGS. 1 and 2) formed by two-part spirals that meet at the apex of the end edge 18 and increase in radius from that point. This portion of the housing contains the fan 11 which is connected to a motor 21 by a drive shaft 22 (see FIG. 3). The motor 21 is connected to, and controlled by, a control board 23 mounted on the back wall 13.

The fragrance source 12 is also carried by the back wall 13 below the fan 11. The construction of this fragrance source 12 will be described in more detail below.

Figure 4:
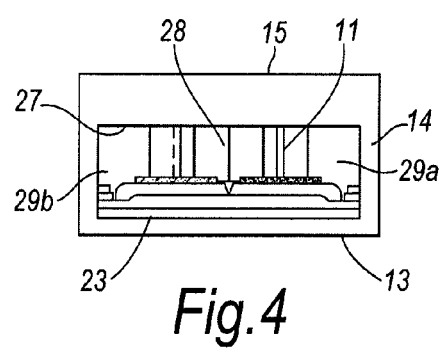
FIG. 4 is a section on the line A-A of FIG. 3.

The front of the housing 10 is closed by the front cover 15 seen in FIGS. 3 and 4. The cover 15 has generally the same shape as the back wall 13 but is provided with an air inlet 26 aligned with the fan 11. In addition, as seen in FIG. 3, the cover is provided with an inwardly slanted wall 27 and a central divider 28. With particular reference to FIGS. 3 and 4, the wall 27 and the divider 28 form a pair of side-by-side ducts 29a, 29b that converge as they extend away from the fan 11 and terminate in respective outlets one of which is shown at 30 in FIG. 3. The position of the divider 28 in relation to the fragrance source 12 will be discussed below.

Figure 5:
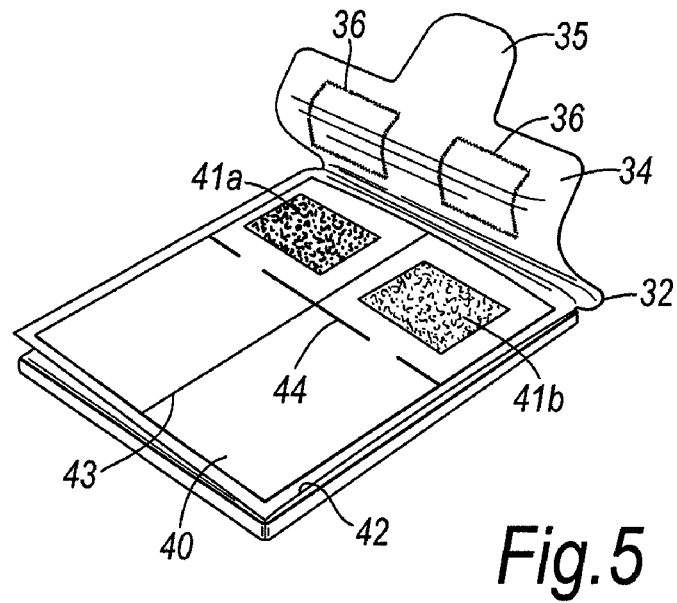
FIG. 5 is a perspective view of the fragrance source of FIGS. 1 to 4.
Figure 6:
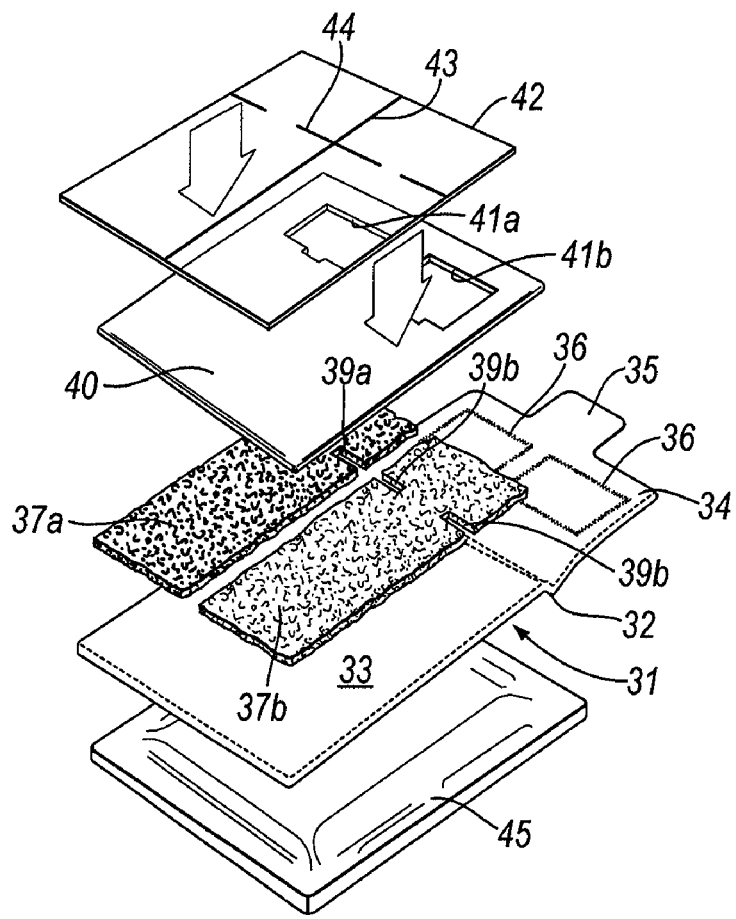
FIG. 6 is an exploded view of the fragrance source of FIG. 5.

The fragrance source 12 is shown in more detail in FIGS. 5 and 6. Referring to those Figures, the fragrance source 12 comprises a back sheet 31 which is of generally rectangular shape and may be formed, for example, from a plastics laminate. The back sheet 31 is provided with a lateral fold line 32 which divides the back sheet 31 into a main portion 33 and a flap 34. The end of the flap 34 is provided with a tab 35 and the surface of the flap on the inner side of the fold line 32 is provided with two adhesive frames 36 whose function will be described below.

First and second strips 37a, 37b of wick material are placed on the inner surface of the main portion 33 of the back sheet 31. Each strip of wick material 37a, 37b is of elongate rectangular shape provided towards one end with a pair of inwardly directed registering notches 39a, 39b whose function will be described below. As seen in FIG. 6, the first and second strips 37a, 37b are arranged side-by-side and parallel to one another.

The first and second strips 37a, 37b are covered by a front sheet 40 that may also be of a plastics laminate and is the same size as the main portion 33 of the back sheet 31. The front sheet 40 is formed towards one edge with two windows 41a, 41b. Each window is in register with a respective shorter portion of an associated one of the first and second strips 37a, 37b between the notches 39a, 39b and the adjacent end of the associated strip 37a, 37b. Of course, the front sheet 40 may be formed in one-piece with the back sheet 31, extending from the edge of the back sheet 31 opposite the fold line 32.

The front sheet 40, when not formed in one-piece with the back sheet, is then connected to the back sheet along lines 42,43,44 by, for example, welding or gluing. The first connection line 42 is a rectangular line extending around the peripheries of the main portion 33 and the front sheet 40 and thus forms a closed chamber between these parts 33,40. The second connection line 43 is a longitudinal line which extends along the gap between the first and second strips 37a, 37b thus sub-dividing the main chamber to form separate chambers each containing a respective strip 37a, 37b. The third connection line 44 is a lateral line extending between the side edges of the main portion 33 and the front sheet 40 with the line 44 extending into the notches 39a, 39b and being interrupted between the notches 39a, 39b. Thus, each sub-chamber containing an associated strip 37a, 37b is divided into a larger portion and a smaller portion separated by a neck with the smaller portion underlying an associated window 41a, 41b.

Each larger portion of each sub-chamber is filled with a respective different liquid fragrance. The flap 34 is folded over the windows 41a, 41b with the adhesive frames 36 sealing around the peripheries of the windows 41a, 41b to close the windows 41a, 41b. Finally, an under surface of the back sheet 31 is mounted on a source of electric power 45. This may be a flat dry cell battery.

Figure 1:
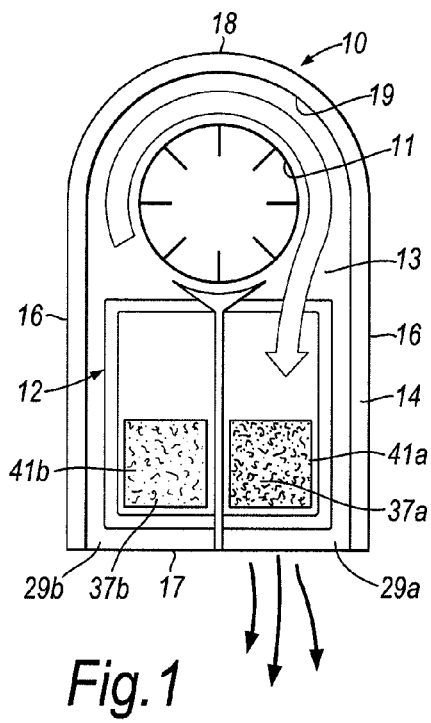
FIG. 1 is a schematic front elevation of a first form of fragrance disperser, a front cover of the disperser being removed to show a fan of the disperser and a fragrance source, the fan rotating in a first sense.

In use, the fragrance source 12 is opened by pulling the tab 35 to open the peelable seal formed by the adhesive frames 36. The fragrance source 12 is then mounted in the housing 10 as briefly described above. In this position, the windows 41a, 41b are, as seen in FIGS. 1 and 2, adjacent the outlets 30 with the divider 28 extending along the longitudinal connecting line 43 so that each window 41a, 41b is in a respective duct 29a, 29b. Each fragrance wicks to the associated window 41a, 41b at a rate controlled both by the characteristics of the strips 37a, 37b and the gaps between the notches 39a, 39b. The source of electric power 45 includes contacts which connect the source of electric power 45 to the control system 23 for the motor 21 of the fan 11.

The motor 21 operates when connected to the source of electric power 45 and the fan 11 rotates in, for example, the clockwise direction shown in FIG. 1. This produces an air flow through the duct 29a associated with the first window 41a and so conveys the associated fragrance to the surrounding atmosphere. The convergence of the duct 29a towards the associated outlet 30 increases the speed of the air as it passes across the window 41a.

After a period of time, the control system 23 reverses the direction of rotation of the fan 11 so that it rotates in an anti-clockwise direction as shown in FIG. 2. The effect of this is to pass air along the duct 29b and across the window 41b so releasing the associated fragrance through the outlet 30 into the surrounding atmosphere.

Figure 7:
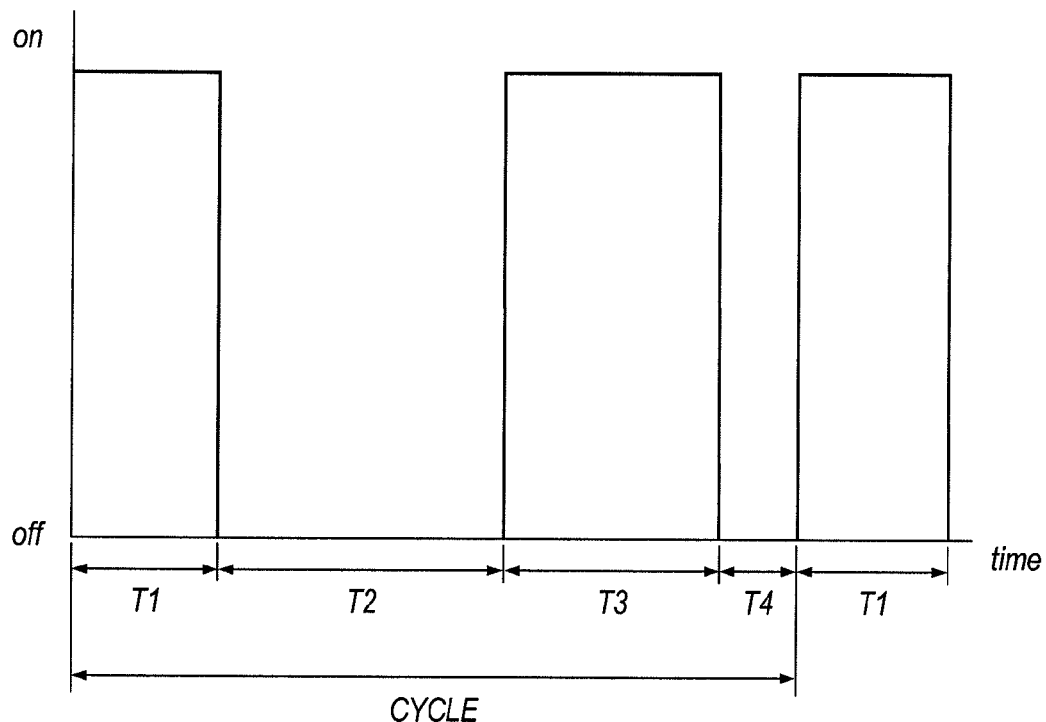
FIG. 7 is a graph of time against operational state for the fragrance disperser of FIGS. 1 to 4.

Referring next to FIG. 7, this shows one mode of operation of the fan 11 under the control of the control system 23. T1 is the time for which the fan 11 rotates in, for example, the clockwise direction. This time is designed to allow the concentration of the first fragrance to reach a maximum. The dwell period T2 is designed to allow the first fragrance to disperse before the second fragrance is emitted. T3 is the time for which the fan rotates in, for example, an anti-clockwise direction to emit the second fragrance and allow it to reach a maximum and T4 is the dwell period that allows the second fragrance to disperse. The time for which each wick is inactive allows the fragrance to wick to the associated window for immediate evaporation when the wick becomes active. As will be seen, these intervals need not be equal. They may be varied depending on the fragrance. There is a known phenomenon called olfactory fatigue where, after a time a person smelling a fragrance at a stable concentration becomes unaware of the smell. This time varies from fragrance to fragrance and the intervals mentioned above may be adjusted in accordance with those times. In addition, the time intervals may be able to be manually adjusted by the user. Further, the control system could be programmed to accommodate small or large rooms or to provide a booster fragrance on demand.

The timing may be altered for different sized rooms in a number of different ways. For example, for a larger sized room, it may be desirable to increase the on times T1, T3 for fragrances 1 and 2 whilst leaving the off times T2, T4 (the dwell periods) unchanged. Alternatively, the cycle could be altered by leaving the on times T1, T3 unchanged but shortening the dwell periods T2, T4. Another possibility is to increase both the on and off times whilst keeping the on/off ratio unchanged. Similarly for smaller rooms it may be desirable to reduce the on times T1, T3 only, or to increase the dwell periods T2, T4 only, or to shorten both whilst maintaining the same ratio.

When the fragrance source 12 is finished, it can be replaced by a new fragrance source 12 on an associated source of electric power 45. The power of the source 45 is matched to the volume of fragrance so that when the power of the source is running low the amount of fragrance remaining is also running low. The control system 23 may monitor battery power and provide an indication when the power is running low so providing an indication that the fragrance is close to exhaustion and requires replacement. The indication may be a visual indication provided, for example, by an LED on the housing 10.

Figure 8:
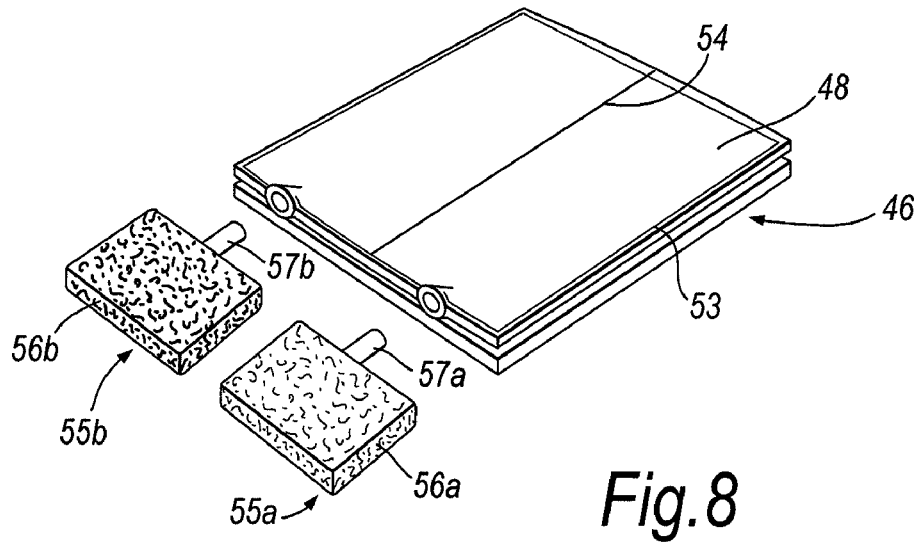
FIG. 8 is a perspective view of a second form of fragrance source for use with the fragrance disperser of FIGS. 1 and 2, two wicks of the source being shown separated from the source for clarity.
Figure 9:
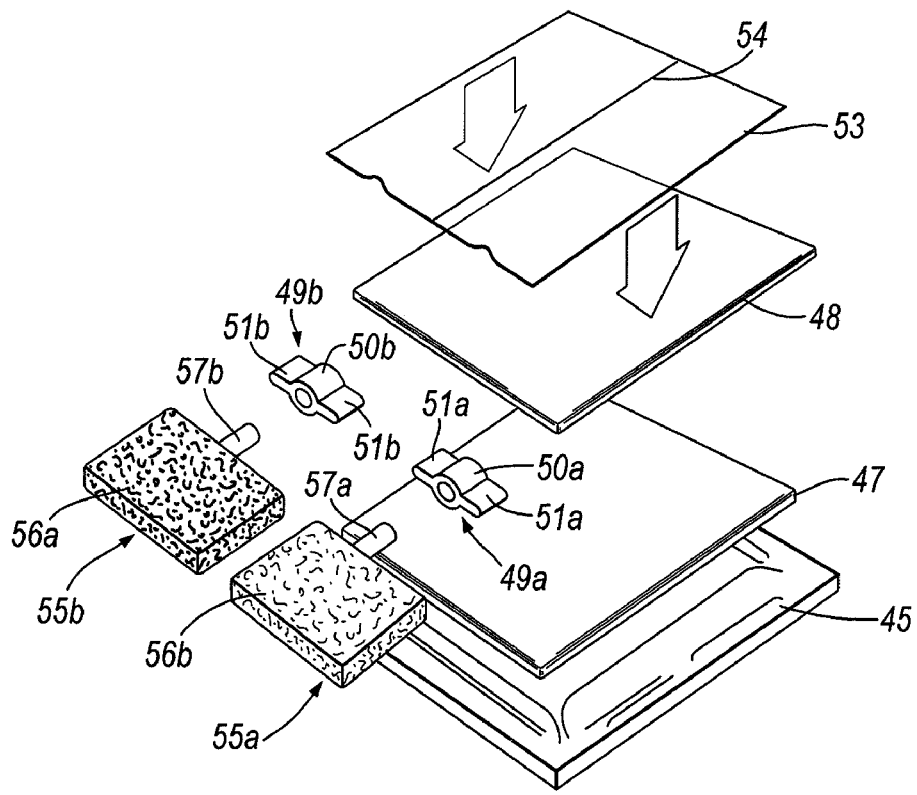
FIG. 9 is an exploded view of the second form of fragrance source of FIG. 8.
Figure 10:
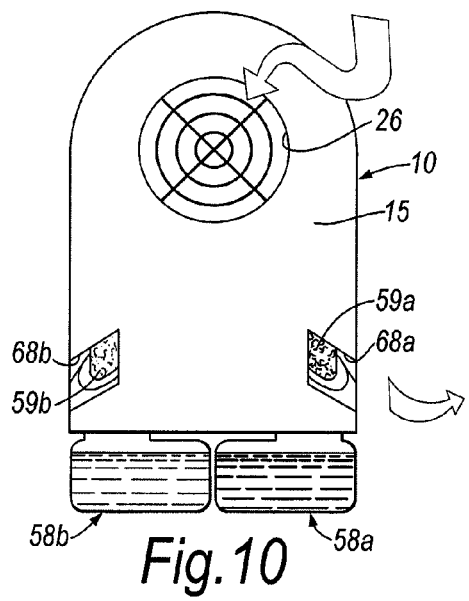
FIG. 10 is a front elevation of a second form of fragrance disperser, and two fragrance sources.

A second form of fragrance source for use with the fragrance disperser of FIGS. 1 and 2 is shown in FIGS. 8 and 9. The second fragrance source 46 is formed by a rectangular back sheet 47 which may be of a plastics laminate and a similar shaped front sheet 48 of the same material. Two valve inserts 49a, 49b are also provided. Each valve insert 49a, 49b is formed by a short section of tube 50a, 50b and a pair of diametrically opposed outwardly extending wings 51a, 51b. Each tube 50a, 50b contains a pierceable seal (not shown).

The back sheet 47 is placed beneath the front sheet 48 with the valve inserts 49a, 49b spaced apart along registering edges of the sheets 47,48. The sheets 47,48 are then connected together along lines 53,54 by, for example, welding or gluing. The first line 53 extends around the peripheries of the back sheet 47 and the front sheet 48 and also connects to the wings 51a, 51b and the tubes 50a, 50b of the valve inserts 49a, 49b. The second line 54 is a longitudinal line extending between the edge of the sheets 47,48 including the valve inserts 49a, 49b and the opposite edge. The back sheet 47 and the front sheet 48 thus formed between them a chamber which is subdivided by the longitudinal line into two sub-chambers. Each chamber contains an associated different liquid fragrance.

The second fragrance source 46 also includes two inserts 55a, 55b. Each insert 55a, 55b is formed by a generally rectangular area of wick material and an elongate capillary connector 57a, 57b projecting from the associated wick material 56a, 56b.

In use, the seals 52 in the valve inserts 49a, 49b retain the associated fragrance in the sub-chambers. When it is wished to use the second fragrance source, each capillary connector 57a, 57b is inserted through an associated seal of a valve insert 49a, 49b to reach the fragrances in the sub-chambers. The fragrances pass along the capillary connectors 57a, 57b to the associated wick materials 56a, 56b where they evaporate.

The second fragrance source 46 may be mounted and used with the fragrance disperser as described above with reference to FIGS. 1 to 4.

Referring next to FIGS. 10 to 14, the second form of fragrance disperser has parts common to the fragrance disperser of FIGS. 1 to 4. Those parts will be given the same reference numerals as the corresponding parts in FIGS. 1 to 4 and will not be described in detail.

In the second fragrance disperser, the fragrance is supplied by two containers 58a, 58b. Each container 58a, 58b is connected to the housing 10 in a manner to be described below and includes a projecting wick 59a, 59b received in an associated shaped duct 60a, 60b formed in the housing 10.

Each container 58a, 58b is formed with a neck 61a, 61b surrounding a mouth 62a, 62b. Each neck has an outwardly directing flange 63a, 63b and the associated wick 59a, 59b extends out of each mouth 62a, 62b. The housing is formed at the lower end edge 17 with two apertures 64a, 64b each for receiving the neck 61 of the associated container 58a, 58b. As seen particularly in FIG. 14, each aperture 64a, 64b includes a retention mechanism for holding the associated container 58a, 58b connected to the housing 10. The retention mechanism is formed by an inwardly directed projection 65 that extends under the flange 63a, 63b of the associated container 58a, 58b and a peg 66 that retracts against a spring 67 as the neck 61a, 61b is pushed into the associated aperture 64a, 64b to allow the flange 63a, 63b to pass the peg 66 and then is forced outwardly by the spring 67 to engage behind the flange 63a, 63b to hold the associated container 58a, 58b in position.

Figure 11:
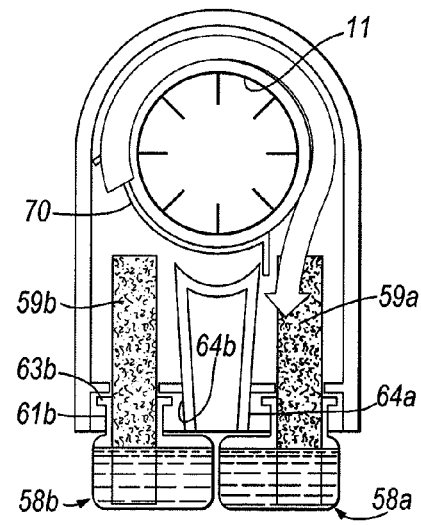
FIG. 11 is a front elevation of the second form of fragrance disperser of FIG. 10 with a front cover removed and showing a fan rotating in one sense.
Figure 12:
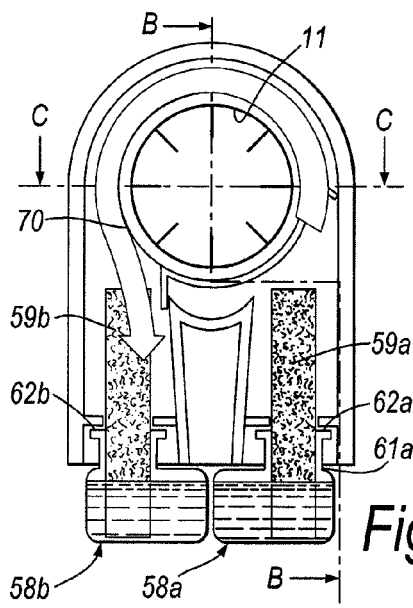
FIG. 12 is a similar view to FIG. 11 but showing the fan rotating in an opposite sense.
Figure 14:
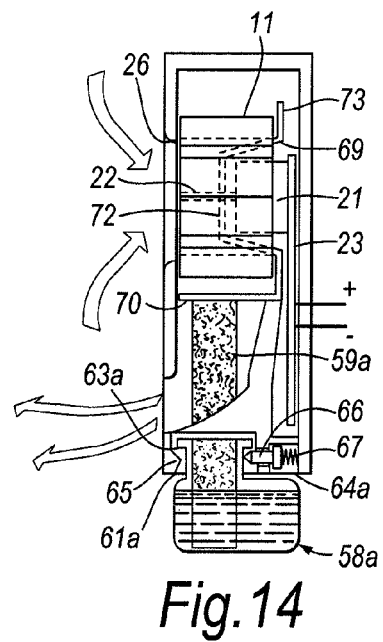
FIG. 14 is a cross-section on the line B-B of FIG. 12.
Figure 13:
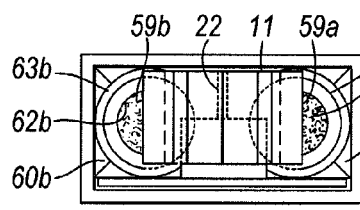
FIG. 13 is an internal view from above of the second form of fragrance disperser.

Each shaped duct 60a, 60b extends from a respective side of the fan 11 initially in a direction tangential to the fan 11. Then, as seen in FIG. 14 the duct 60a, 60b turns through 90° to terminate in an outlet 68a, 68b on the cover 15. As seen in FIGS. 11, 12 and 14, each wick 59a, 59b extends along the associated duct 60a, 60b to terminate adjacent the periphery of the fan 11. The fan 11 is associated with a shutter 69 which is carried on the drive shaft 22 and includes an arcuate wall 70. As seen in FIG. 11, when the fan 11 rotates in a clockwise direction, the wall 70 of the shutter 69 closes the duct 60b and leaves the duct 60a open so minimizing the volume of air leaving the duct 60b. When the fan 11 rotates in an anti-clockwise direction, the wall 70 of the shutter 69 closes the other duct 60a leaving the duct 60b open and so minimizing the volume of air leaving the duct 60a.

The construction and operation of the shutter 69 will be described in more detail below.

In use, the second fragrance disperser described above with reference to FIGS. 10 to 14, operates broadly as described above with reference to FIGS. 1 to 4. Air from the fan passes along one or other of the shaped ducts 60a, 60b and evaporates fragrance from the associated wick 59a, 59b which then passes out of the associated outlet 68a, 68b into the surrounding atmosphere. The shape of the duct 60a, 60b ensures that air from the fan 11 does not pass simply axially along the wicks 59a, 59b. Rather, the shape of the ducts 60a, 60b results in a circumferential flow of air around the wicks 59a, 59b. This results in more efficient evaporation of fragrance from the wicks 59a, 59b.

Power for the motor 21 is provided from an external power supply such as a battery (not shown) or a source of mains power.

When a container 58a, 58b is empty, it can be released from the retention mechanism and replaced by a fresh container.

Figure 15:
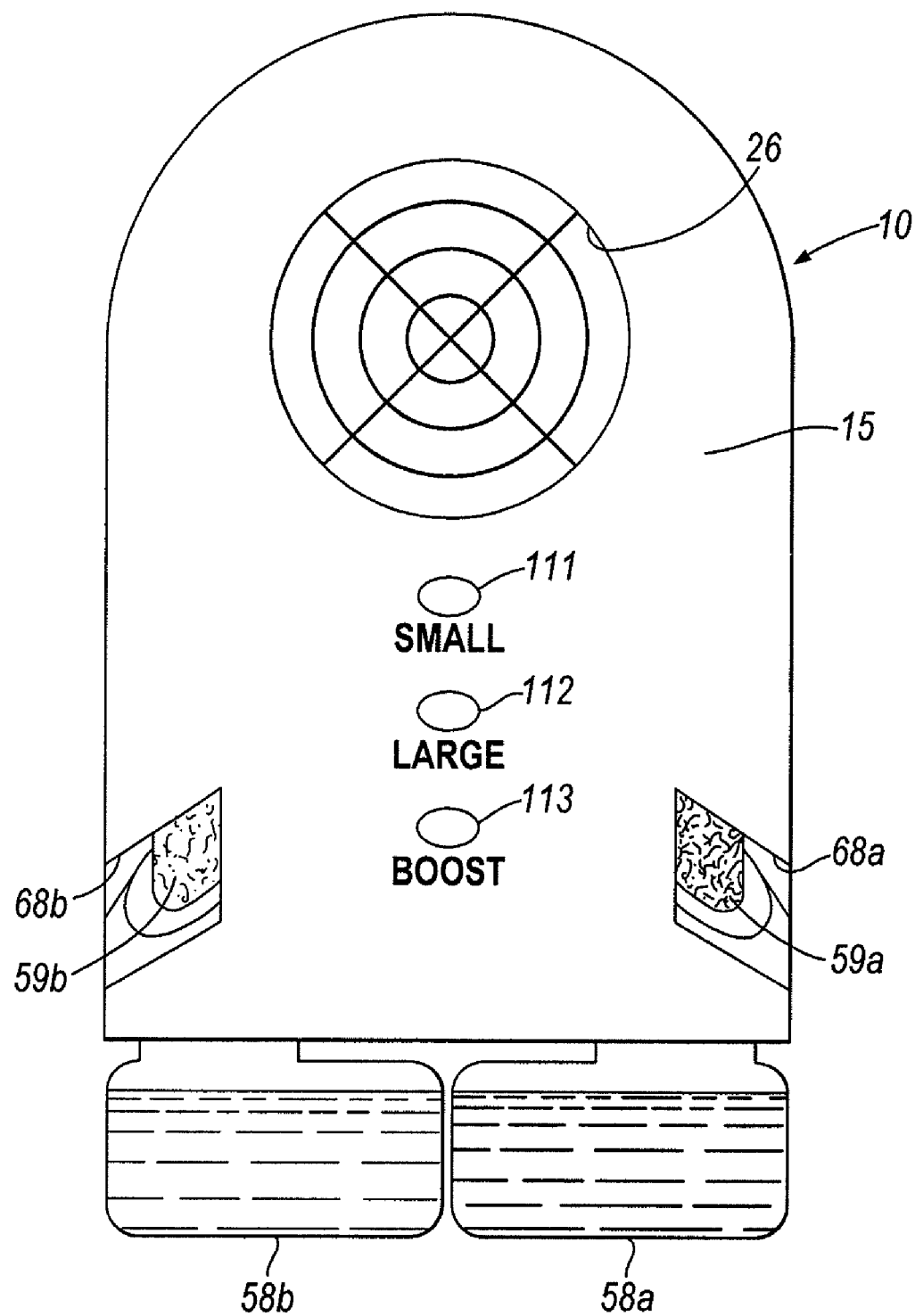
FIG. 15 is a similar view to FIG. 10 showing the second fragrance disperser provided with buttons that allow different modes of operation.

Referring now to FIG. 15, parts common to FIG. 15 on the one hand and FIGS. 10 to 14 on the other hand will be given the same reference numerals and will not be described in detail. In this arrangement the housing 10 is provided with three control buttons 111,112,113. On pressing the button 111, the timing protocol is altered to be suitable for smaller rooms. Pressing the button 112 alters the timing protocol to be suitable for larger rooms. Pressing the button 113 alters the timing protocol for a set limited period of time. For that limited period of time, the volume of fragrance emitted is increased. This provides a boost of fragrance. Alternatively, instead of changing the time periods for which the fan 11 operates, the speed of the fan 11 could be increased or decreased to alter the volume of fragrance emitted. This could be achieved by the varying power supplied to the motor.

Other means for controlling the volume of fragrance emitted will now be described with reference to FIGS. 16 to 19, in which parts common to FIGS. 10 to 15 on the one hand and to FIGS. 16 to 19 on the other hand will be given the same reference numerals and will not be described in detail.

Figure 16:
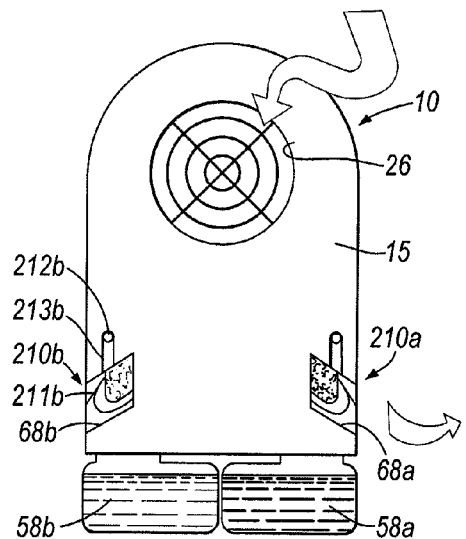
FIG. 16 is a similar view to FIG. 10 showing the second fragrance disperser with shutters that control the volume of fragrance dispersed, FIG. 17 corresponds to FIG. 16 but shows one of the shutters in a fully open position and the other in a partially closed position.
Figure 17:
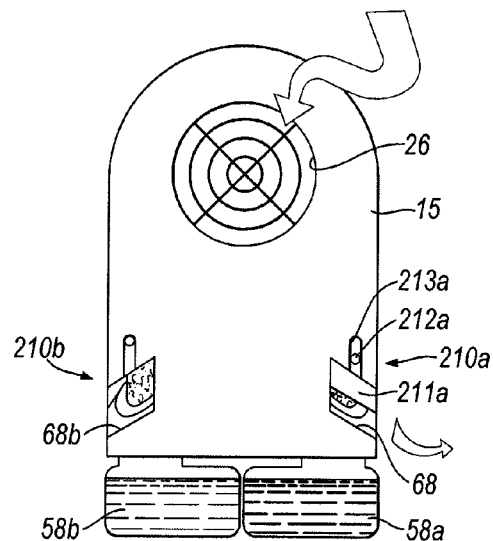

Referring first to FIGS. 16 and 17, the size of each duct opening 68a, 68b is controlled by a respective shutter assembly 210a, 210b. Each assembly 210a, 210b comprises a shutter 211a, 211b to which is connected a peg 212a, 212b which is slidably movable in a vertical slot 213a, 213b in the front cover 15 of the disperser, such that when the peg 212a, 212b is at the top of the slot 213a, 213b the shutter is in a fully open position and the duct opening 68a, 68b is a maximum size, and when the peg is at the bottom of the slot the shutter is in a fully closed position and the duct opening is a minimum size. This may correspond to completely closing off the duct opening 68a, 68b.

Each shutter assembly 210a, 210b may be controlled independently to control the relative volumes of each fragrance emitted. In FIG. 16, both shutters 211a, 211b are shown in the fully open position, and the respective pegs 212a, 212b can be seen at the top of each respective associated slot 213a, 213b. In FIG. 17, the right-hand shutter assembly 210a is shown in an intermediate position, the shutter 211a partially restricting the associated duct opening 68a to reduce the volume of fragrance emitted from the associated container 58a. In the same Figure, the left-hand shutter assembly 210b is in the fully open position. Thus, for a given fan speed, or a given time for which the fan 11 is operational, a greater proportion of fragrance will be emitted from container 58b than from container 58a.

As described above, each shutter assembly is adjusted manually by means of the respective peg 212a, 212b. Alternatively, the shutters 211a, 211b may be controlled electronically, in which case the pegs 212a, 212b and the slots 213a, 213b may be disposed of.

Figure 18:
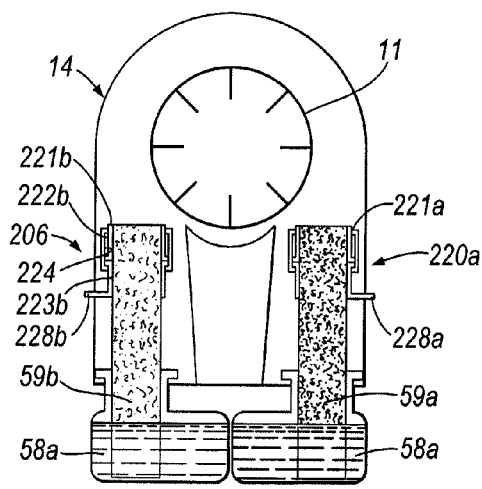
FIG. 18 is a similar view to FIG. 11 showing the second fragrance disperser with wick cover assemblies that control the volume of fragrance dispersed, FIG. 19 corresponds to FIG. 18 but shows one of the wick covers covering a wick to a minimum degree and the other covering another wick to a maximum degree.
Figure 19:
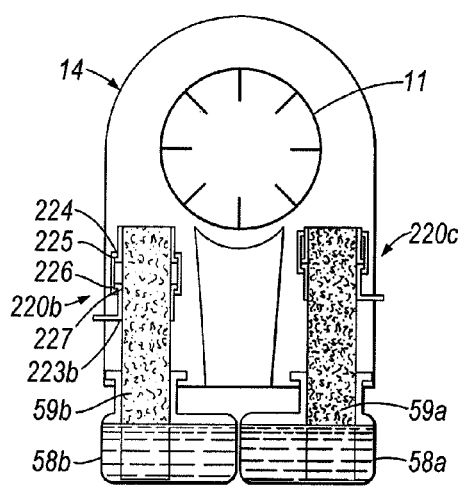

Referring now to FIGS. 18 and 19, the exposed surface area of each wick 59a, 59b is controlled by a respective wick cover assembly 220a, 220b. Each wick cover assembly 220a, 220b comprises a cap 221a, 221b, a cover 222a, 222b and a slider 223a, 223b. The cap 221a, 221b is substantially cylindrical and is mounted on the upper surface of the associated wick 59a, 59b and includes at its lower end an annular shoulder 224. The cover 222a, 222b is substantially cylindrical and includes at each of its upper and lower ends an inwardly projecting annular lip 225 and 226 respectively. The slider 223a, 223b is also substantially cylindrical and includes at its upper end an annular shoulder 227 and near its lower end and a horizontally projecting peg 228a, 228b. The peg 228a, 228b is slidably movable in a vertical slot (not shown) in the side wall 14 of the disperser. The slider 223a, 223b is slidably mounted on the associated wick 59a, 59b and is connected to the cover 222a, 222b in the region of the annular shoulder 227 of the slider and the lower annular lip 226 of the cover. In this way, the cover 222a, 222b is slid over the cap 221a, 221b by virtue of a corresponding sliding movement of the slider 223a, 223b over the wick 59a, 59b, which is, in turn, controlled manually by sliding the associated peg 228a, 228b within its associated slot. The cover 222a, 222b and the slider 223a, 223b could alternatively be combined as a single part.

In a first position, corresponding to that shown for both wick cover assemblies 220a, 220b in FIG. 18 and for the right-hand wick cover assembly 220a in FIG. 19, the slider 223a, 223b is in an upper position in which the annular shoulder 227 of the slider 223a, 223b abuts the annular shoulder 224 of the cap 221a, 221b. In this position, the cover 222a, 222b substantially entirely overlaps the cap 221a, 221b, and the associated wick 59a, 59b is thus exposed to a maximum extent.

In a second position, corresponding to that shown for the left-hand wick cover assembly 220b in FIG. 19, the slider 223b is in a lower position in which the upper lip 225 of the cover 222b abuts the annular shoulder 224 of the cap 221b. In this position, the cover 222b extends beyond the cap 221b and covers a portion of the wick 59b. In this second position, the wick is thus exposed to a minimum extent, and for a given fan speed or a given time for which the fan 11 is operational, a lesser proportion of fragrance will be emitted than when the wick cover assembly 220a, 220b is in the first position, by virtue of the reduced exposed wick surface area. The sliders 223a, 223b may be positioned intermediate the first and second positions, and each is independently controllable to control the relative volumes of fragrance emitted from each respective container 58a, 58b.

As with the shutter assemblies 210a, 210b of FIGS. 16 and 17, control of the wick cover assemblies 220a, 220b need not be manual. Indeed, it may be automatic, or electronic, in either case there being no need for the provision of the pegs 228a, 228b and their associated slots in the side wall 14.

Figure 20:
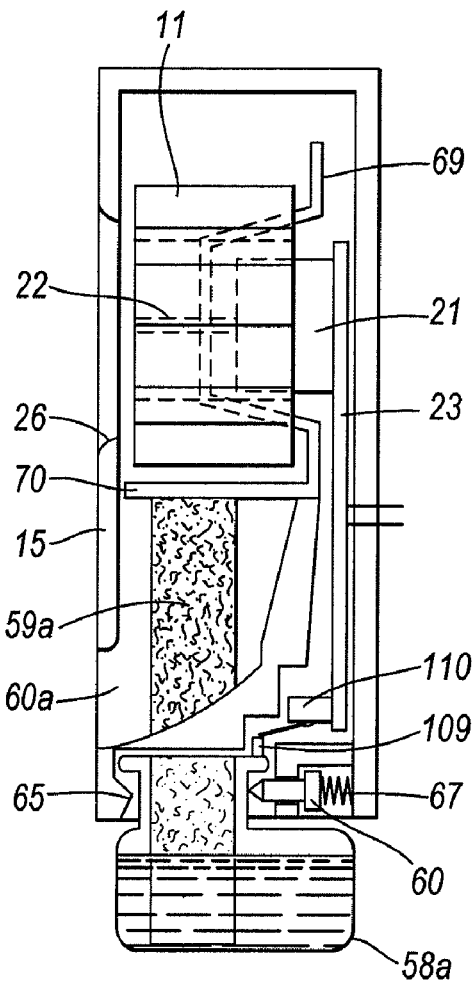
FIG. 20 is a similar view to FIG. 14 but with the fragrance source including a peg and the fragrance disperser including a microswitch operable by the peg.
Figure 21:
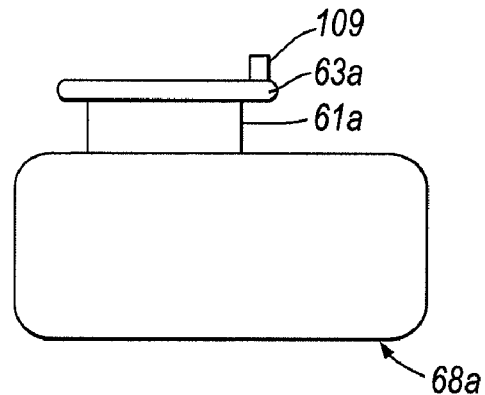
FIG. 21 is a side view of a fragrance source of FIGS. 9 to 13 and including a peg but with the fragrance and wick removed.
Figure 22:
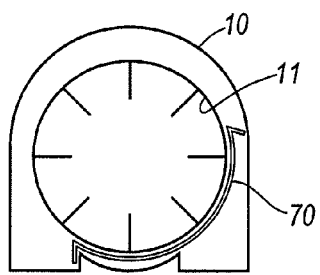
FIG. 22 is a schematic view of the fan of the second form of fragrance disperser together with a shutter.

Referring next to FIGS. 20 and 21, the disperser of FIGS. 10 to 14 may be modified so that the operation of the disperser is varied in accordance with information derived from the associated containers 58a, 58b. Parts common to FIGS. 20 and 21 on the one hand and to FIGS. 10 to 14 on the other hand are given the same reference numerals and are not described in detail. In this arrangement, the flange 63a, 63b on the neck 61a, 61b of each container 58a, 58b is provided with a peg 109. When the container 58a, 58b is engaged with the housing 10, the peg 109 engages an associated microswitch 110. The microswitch 110 passes a signal to the control system 23 that modifies the operation of the control system 23. For example, when a signal is received from the microswitch, the relevant cycle times may be altered in comparison with the cycle times when the peg 109 is absent.

Other arrangements are possible. For example, the container may include a readable microchip or bar code that provides information to the control system 23 for adjusting the operation of the fan 11.

Figure 23:
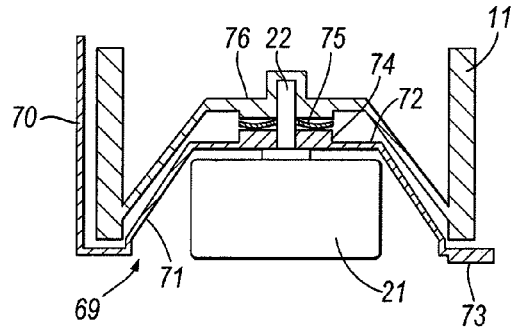
FIG. 23 is a schematic cross-section of the fan and shutter of FIG. 22 showing the parts interconnected by a frictional clutch.

Referring next additionally to FIGS. 22 to 25, these Figures illustrate various modes of operation of the shutter 69. As seen in FIG. 23, the shutter 69 comprises a generally frusto-conical portion 71 with the narrower end closed by an end wall 72. The drive shaft 22 passes through this end wall and is coaxial with the axis of the frusto-conical portion 71. A peripheral flange 73 extends outwardly of and around the wider end of the frusto-conical portion 71 and the wall 70 extends around a portion of this flange 73. In order to counter balance the wall 70, the diametrically opposite portion of the flange 73 may be thickened so that the shutter 69 is in static balance around the drive shaft 22.

In its simplest form of operation, the shutter 69 may be rotated only by the air flow generated by the fan 11. When the fan 11 is rotating in an anti-clockwise direction, there will be a corresponding anti-clockwise flow of air and, due to the balance of the shutter 69, this may be sufficient to rotate the shutter to the position shown in FIG. 11. Likewise, when the fan 11 rotates in a clockwise direction, there is a corresponding clockwise rotation of air which moves the shutter 69 to the position shown in FIG. 12.

There may, however, be cases where this movement cannot be achieved reliably by the use of air alone. In this case, and referring to FIG. 23, in an alternative arrangement, a felt washer 74 and a crimped washer 75 are provided on the drive shaft 22 between the end wall 72 of the shutter 69 and a mounting boss 76 of the fan 11 which is connected to drive shaft 22. In this arrangement, when the motor 21 rotates in one direction, the rotational movement of the fan 11 is transmitted frictionally by the washer 74, 75 to the shutter 69 so rotating the shutter 69 in the same sense as the fan. The arrangement works in whichever direction the motor 21 is rotated.

Figure 24:
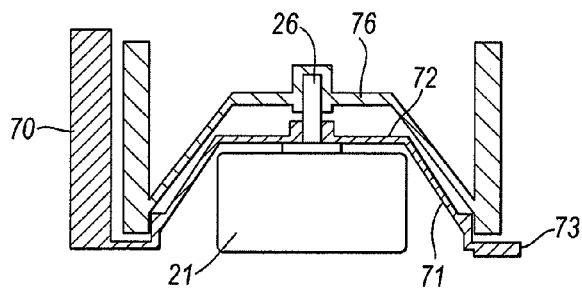
FIG. 24 is a schematic cross-section of the fan and shutter of FIG. 22 showing the parts interconnected by a centrifugal clutch.
Figure 25:
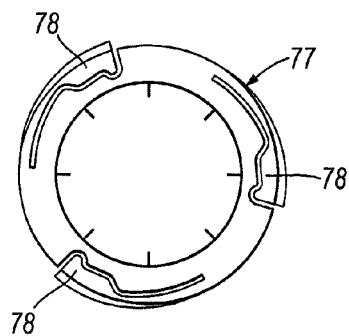
FIG. 25 is a plan view of a first clutch part of the centrifugal clutch of FIG. 24.
Figure 26:
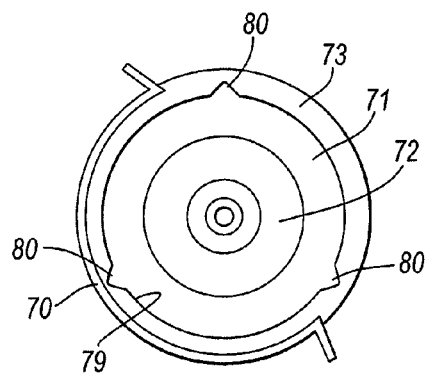
FIG. 26 is a plan view of a second clutch part of the centrifugal clutch of FIG. 24.

Another possibility is shown in FIGS. 24, 25 and 26. In this arrangement, the fan 11 carries a first clutch part 77 shown in FIG. 25. This clutch part 77 includes three arcuate arms 78 which, as the fan 11 rotates, move from the full line position shown in FIG. 25 outwardly to the dotted line position shown in that Figure. The shutter 69 includes a second clutch part 79 (see FIG. 26) which includes three outwardly directed equi-angularly spaced projections 80. When the arms 78 are in the full line position shown in FIG. 25, they engage these projections 80 so locking the first and second clutch parts 77,79 together and thus rotating the shutter 69 with the fan 11. As the speed of the fan 11 increases, the arms 78 move to the dotted line position shown in FIG. 25 where they are disengaged from the projections 80 so allowing the fan 11 to rotate independently of the shutter 69 with the shutter 69 being maintained in position by air flow (and possibly friction).

It will be appreciated that these are only some of the ways in which the shutter 69 can be moved. Other ways are possible.

Referring next to FIGS. 27 to 31, the third fragrance disperser has parts common with the second fragrance disperser of FIGS. 10 to 14. Those common parts will be given the same reference numerals and their construction and operation will not be described in detail.

The third fragrance disperser includes two fragrance sources 81a, 81b in which the wick is surrounded by an outlet formed by part of the source.

Referring particularly to FIGS. 28 and 29, each fragrance source 81a, 81b includes a container 82a, 82b holding a liquid fragrance and including an integral outlet 83a, 83b. Each outlet 83a, 83b is formed at its end remote from the container 82a, 82b with an entrance 84a, 84b and, at a point in the outlet 83a, 83b adjacent the associated container 82a, 82b, each outlet 83a, 83b is formed with an exit 85a, 85b (see FIG. 30). As seen in FIGS. 27 and 30, these exits 85a, 85b are aligned with respective apertures 86a, 86b in the cover 15 of the housing 10. Each outlet 83a, 83b contains an upper portion of an elongate strip shaped wick 87a, 87b whose lower end is immersed in the fragrance in the container 82a, 82b. Each outlet is a snap fit in an associated shaped duct 60a, 60b of the housing 10.

In use, rotation of the fan 11 in a clockwise direction produces an air flow which is forced through the first duct 60a and enters the entrance 84a of the outlet 83a of the associated fragrance source 81a. The air then passes over and around the wick 87a releasing fragrance which then passes through the exit 85a and through the aperture 86a of the cover 15 to the surrounding atmosphere. Anti-clockwise rotation of the fan 11 produces, as seen in FIG. 25, a flow of air through the entrance 84b of the outlet 83b, past the associated wick 87b and then through the exit 85b and the cover aperture 86b.

The cover apertures 86a, 86b may be provided with respective shutter assemblies as described above with reference to FIGS. 16 and 17.

When a fragrance source 81a, 81b is empty, it can be replaced by a fresh fragrance source.

In this embodiment, the wick 87a, 87b is packaged within and protected by the outlet 83a, 83b. The air duct is part of the fragrance source 81a, 81b and is thus a consumable. Each wick 87a, 87b may be provided with a wick cover assembly similar to those described above with reference to FIGS. 18 and 19, but adapted for consumable fragrance sources.

Figure 32:
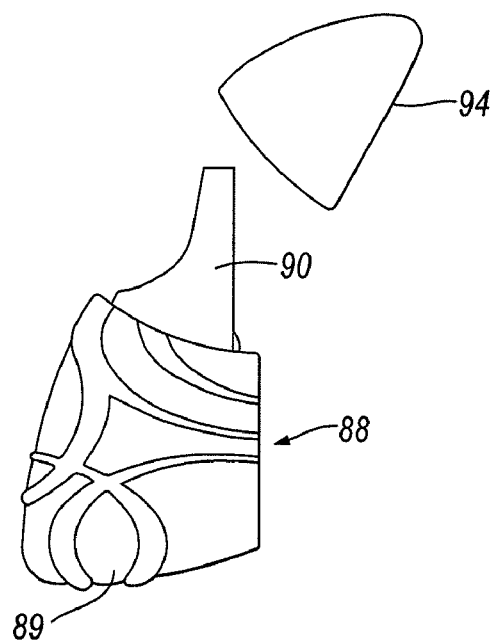
FIG. 32 is a side elevation of a fragrance source for use with the third forms of fragrance disperser, a cap of the source being removed.
Figure 33:
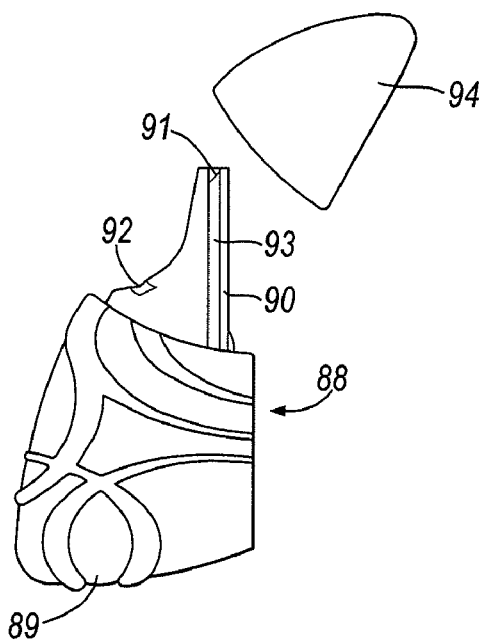
FIG. 33 is a similar view to FIG. 32 but showing the internal structure of an outlet to the source.
Figure 34:
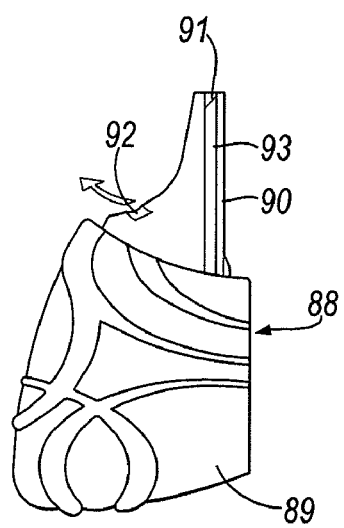
FIG. 34 is a similar view to FIG. 32 but showing a flow of air through the outlet to the fragrance source.

Referring next to FIGS. 32, 33 and 34, there is shown a fragrance source of a kind for use with the third form of fragrance disperser described above with reference to FIGS. 27 to 31. The fragrance source is formed by a container 88 comprising a reservoir 89 and an outlet 90. The parts may be formed from any suitable material such as a plastics material or glass. As seen in FIG. 34, the outlet 90 is formed at its end remote from the reservoir 89 with an entrance 91 and, at a point in the outlet 90 adjacent the reservoir 89, the outlet 90 is formed with an exit 92. A wick 93 leads from the reservoir 89 and terminates in the outlet 90 adjacent the entrance 91.

The reservoir 89 contains a fragrance. A shaped cap 94 covers the outlet 90.

This container 88 can be used with the fragrance disperser of FIGS. 27 to 31. The cap 94 is removed and the outlet 90 inserted into the housing 10. Air is then passed through the outlet 90 via the entrance 91 as described above. The air then leaves via the exit 92.

It will be seen from FIGS. 27 to 31, that, when mounted on the housing 10, the fragrance sources 81a, 81b are side-by-side. It will be appreciated that these two fragrance sources 81a, 81b, may contain different fragrances. Not all pairs of fragrances are perceived by the nose as being complementary and it is plainly desirable to avoid combinations that are perceived as non-complementary.

Figure 35:
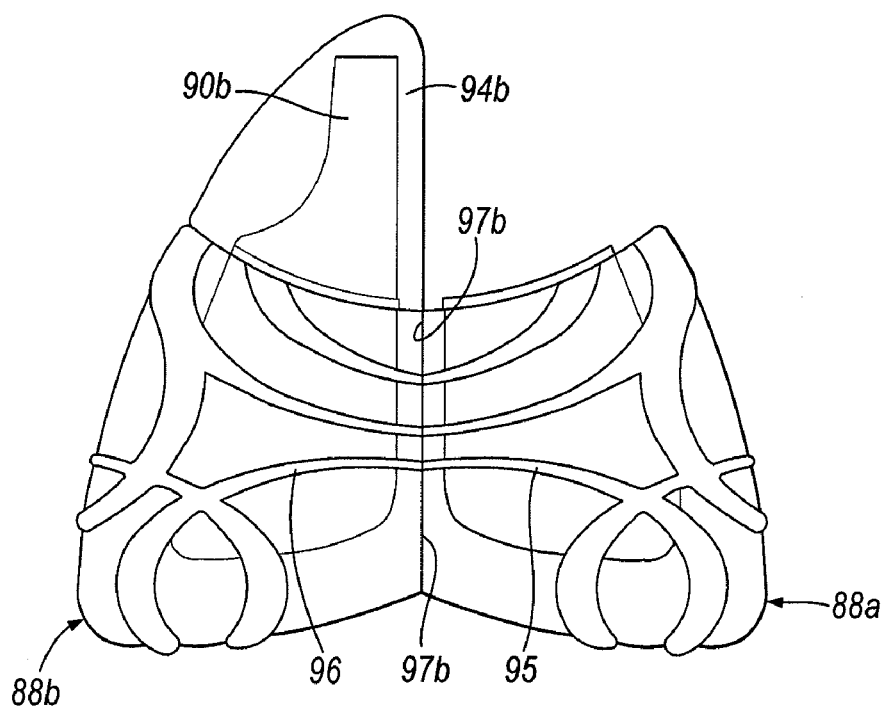
FIG. 35 is a side elevation of a fragrance source of the kind shown in FIGS. 32 to 34 adjacent a second such source shown with the cap and outlet omitted.
Figure 36:
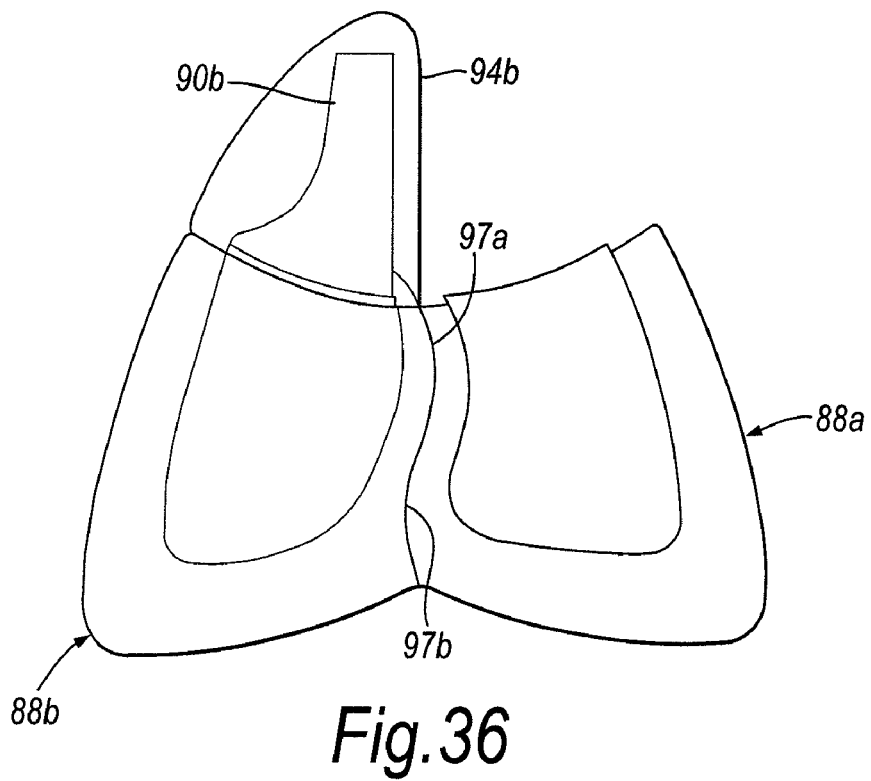
FIG. 36 is a side elevation of a modified form of the fragrance source of FIGS. 32 to 34 adjacent a second such source with the cap and outlet omitted.

Proposals for overcoming this are shown in FIGS. 35 and 36.

Referring first to FIG. 35, two containers 88a, 88b are provided of the kind described above with reference to FIGS. 32 to 34. A first container 88a is provided with a surface pattern 95 that forms a continuous pattern with a corresponding pattern 96 on the second container 88b, with the pattern being continuous across the junction between adjacent side surfaces 97a, 97b of the containers 88a, 88b. These containers 88a, 88b are arranged to contain complementary fragrances (i.e. fragrances that are complementary in an olfactory sense) and any container containing a non-complementary fragrance has a different pattern which does not match the pattern of either of the containers in FIG. 30. Thus, if a container including a non-complementary fragrance is used with one of the containers illustrated in FIG. 30, the lack of matching pattern will be readily apparent. It will be appreciated that this effect need not be provided by a raised pattern. Inset patterns may be used or simply print effects.

Another possibility is provided by the arrangement of FIG. 36. In this Figure, one side surface 97a of one container 88a has a non-planar shape which is complementary with a non-planar shape of the side surface 97b of the other container 88b containing a complementary fragrance so that the side surfaces 97a, 97b interlock when the containers 88a, 88b are placed side-by-side in the housing 10. Containers holding non-complementary fragrances are provided with different side surface configurations and so will not be able to interlock and will thus not be able to be used.

Figure 37:
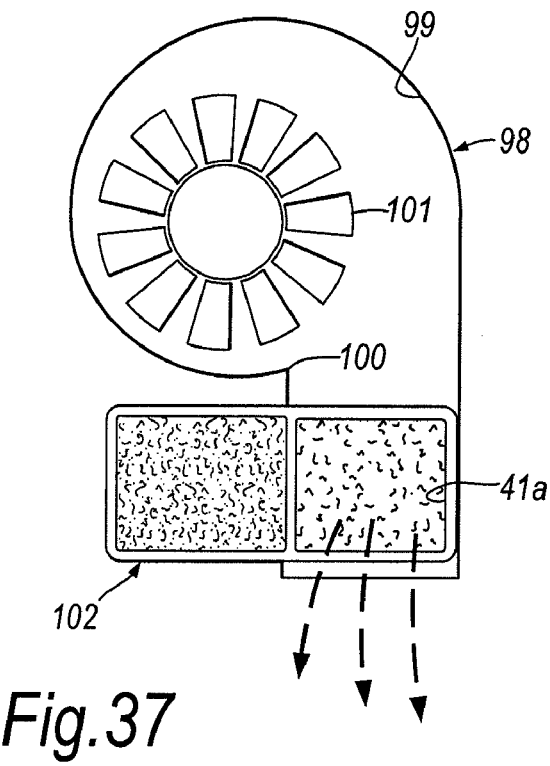
FIG. 37 is a schematic side elevation of a fourth form of fragrance disperser including a fan and a source of a single fragrance.

The use of a fan to disperse fragrance need not be confined to the dispersal of two fragrances. Referring next to FIG. 37, a fourth form of fragrance disperser is formed by a housing 98 including a chamber having an inner wall 99 formed as a spiral of increasing radius and leading to an outlet 100 extending tangentially from the wall 99. A fan 101 is mounted in the housing 98 and is driven by a motor (not shown). The outlet contains a fragrance source 102 which may be formed by a half of the fragrance source described above with reference to FIGS. 5 and 6. The window 41a lies within the outlet 100 and rotation of the fan passes air across the window 41a to evaporate the fragrance.

In this embodiment, the fan 101 rotates in one direction only and so can be designed to be of high efficiency. The motor is controlled by a manually operated switch to give fragrance on demand. The motor is powered by a source of electric power of the kind described above with reference to FIGS. 5 and 6.

Figure 38:
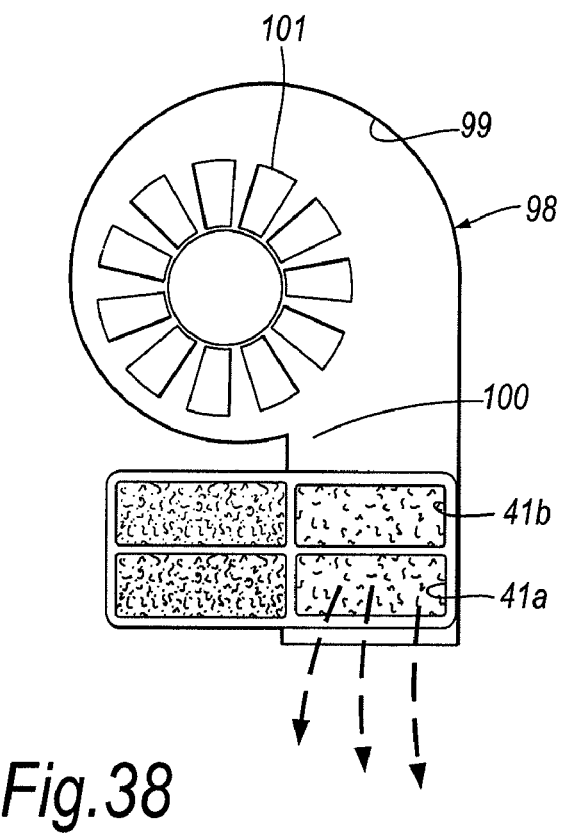
FIG. 38 is a similar view to FIG. 37 but with the source having two fragrances.

A variation of this embodiment is shown in FIG. 38. Parts common to FIG. 37 and to FIG. 38 are given the same reference numerals and are not described in detail.

In the embodiment of FIG. 38, the fragrance source is identical to the fragrance source of FIGS. 5 and 6 with both windows 41a, 41b being within the outlet 100. The two fragrances in the fragrance source are chosen to combine at the point of dispersion to give a desired single fragrance. This arrangement is particularly useful where the desired fragrance is fowled of components that degrade if kept together. By combining them only at the point of dispersion, this degradation is avoided.

Figure 39:
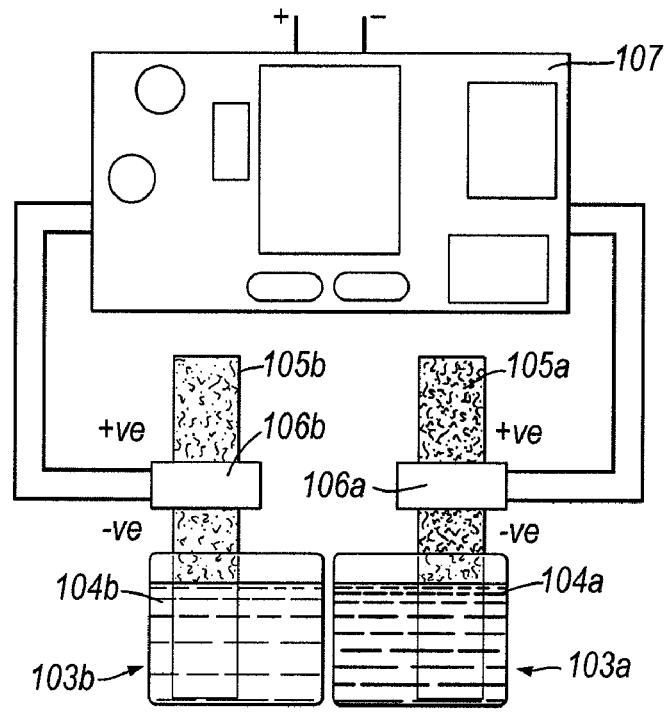
FIG. 39 is a schematic view of a fifth form of fragrance disperser including two sources of fragrance dispersed by heat and a control system.

Of course, the fragrance source of FIGS. 8 and 9 could also be used with either of these embodiments. Also, the size of the window 41a, 41b may be controlled by an arrangement similar to that described above with reference to FIGS. 16 and 17.

Where two fragrances are to be evaporated alternately, the evaporation need not be by a forced air flow. Referring next to FIG. 39, a fifth form of fragrance disperser includes two sources of fragrance 103a, 103b. Each source 103a, 103b includes a container 104a, 104b and an associated wick 105a, 105b projecting from the associated container 104a, 104b. Each wick 105a, 105b is surrounded by an associated heater 106a, 106b. Each heater 106a, 106b is connected to a control board 107 which in turn is connected to an external power supply (not shown). The control board passes current to the heaters 106a, 106b in accordance with a predetermined programme. As each heater receives current, its temperature rises and this in turn evaporates fragrance from the associated wick 105a, 105b. The control board may be arranged to provide a cycle of evaporation similar to that shown in FIG. 7. In addition, controls may be provided for different timing protocols as described above with reference to FIG. 15. Also, varying the power supply varies the temperature of the heater and thus the volume of fragrance evaporated.

Figure 40:
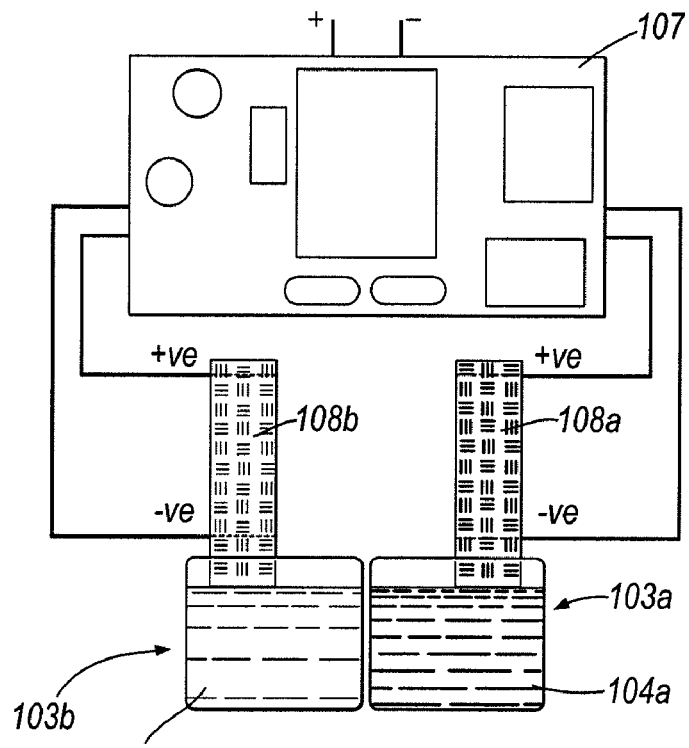
FIG. 40 is a similar view to FIG. 39 but showing an alternative method of dispersing the fragrances by heat.

An alternative arrangement is shown in FIG. 40. Parts common to FIGS. 39 and 40 are given the same reference numerals and are not described in detail. In this embodiment, the heaters 106a, 106b are omitted and the wicks 108a, 108b are formed of or include an electrically conductive material which is connected to the control board 107. Accordingly, when electrical current is supplied to either wick 108a, 108b, the temperature of the wick is raised to evaporate fragrance.

Figure 41:
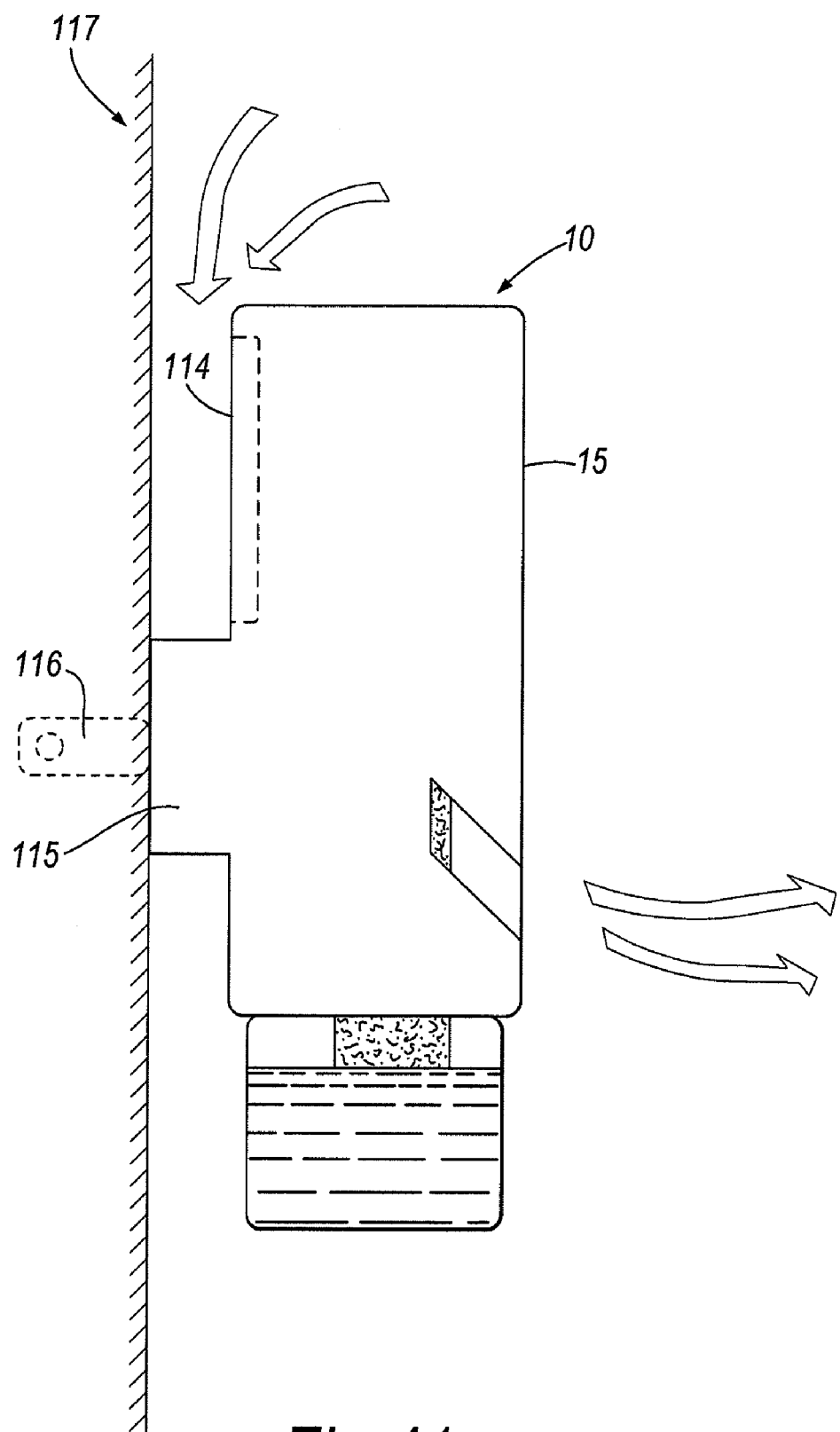
FIG. 41 is a schematic view of a fragrance disperser of any of the kinds shown in FIGS. 1 to 4 or FIGS. 10 to 19 or FIGS. 27 to 31 and mounted on a vertical surface.

Any of the fragrance dispersers described above with reference to FIGS. 1 to 4 or 10 to 19 or 27 to 31 may be mounted on a wall. Referring next to FIG. 41, parts common to those Figures and to FIG. 41 will not be described in detail and will be given the same reference numerals. Referring to FIG. 41, the cover 15 is continuous with the air inlet 26 omitted. Instead, an air inlet 114 is provided on the back wall 13. In addition, an electrical connector 115 projects from the back wall 13 and includes pins, one of which is shown at 116 received in an electrical socket on a vertical surface 117 such as a wall to support the fragrance disperser and provide electrical power. The location of the air inlet 114 is a safety feature since it prevents, for example, fingers being inserted into the path of the fan 11.

We claim:

1. A method of emitting fragrances, the method comprising the steps of:
providing a fragrance dispenser having first and second sources of fragrance, an air flow means for generating a flow of air to release fragrance from the first and second sources of fragrance, and a control means for controlling the release of the first and second sources of fragrance;
emitting the first fragrance for a first period of time;
emitting the second fragrance for a second period of time following the first period of time, wherein no other source of fragrance is emitted therebetween; and
alternatingly emitting the first and second fragrances by repeating the steps of emitting the first and second fragrances with no other source of fragrance emitted therebetween.

2. The method of emitting fragrance of claim 1, further including the step of causing release of the two fragrances continuously.

3. The method of emitting fragrance of claim 1, further including the step of causing release of fragrances with a time interval between successive releases in which no fragrance is released.

4. The method of emitting fragrance of claim 1, further including the step of causing times of release of the two fragrances to be equal.

5. The method of emitting fragrance of claim 1, further including the step of causing times of release of the two fragrances to be unequal.

6. The method of emitting fragrance of claim 1, further including the step of causing a rate of release of the two fragrances to be different.

7. The method of emitting fragrance of claim 6, further including the step of causing a) release of the two fragrances with a time interval between successive releases, and b) the different rates of release of the two fragrances by altering the time periods of release.

8. The method of emitting fragrance of claim 6, further including the step of causing a) release of the two fragrances with a time interval between successive releases, and b) the different rates of release of the two fragrances by altering the time interval between successive releases.

9. The method of emitting fragrance of claim 6, further including the step of causing the different rates of release of the two fragrances by altering both times of release of the two fragrances and time intervals between release of the two fragrances such that a ratio of time release to time interval is unchanged.

10. The method of emitting fragrance of claim 6, further including the step of causing an increase in the different rates of release of the two fragrances relative to a datum rates of release.

11. The method of emitting fragrance of claim 6, further including the step of providing a manually operable means for operating the control means to cause the different rates of release of the two fragrances.

12. The method of emitting fragrance of claim 11, further including the steps of providing a fragrance flow path outlet and providing the control means with a manually adjustable shutter for varying a size of the flow path outlet.

13. The method of emitting fragrance of claim 1, further including the step of providing at least one of the sources of fragrance with a means for controlling the control means to alter the release of the two fragrances.

14. The method of emitting fragrance of claim 13, further including the step of providing the at least one source of fragrance with a pin, wherein the control means includes a switch engagable by the pin such that engagement of the pin with the switch causes the control means to alter the release of the fragrances.

15. The method of emitting fragrance of claim 1, further including the step of providing each source of fragrance with a fragrance container comprising a reservoir for receiving liquid fragrance and an outlet to the reservoir, the outlet defining a path for a flow of air to release fragrance in the reservoir.

16. The method of emitting fragrance of claim 15, further including the step of providing the outlet with a passage for the air flow and having an entrance at an end of the outlet remote from the reservoir and an exit for fragrance laden air adjacent the reservoir.

17. The method of emitting fragrance of claim 16, further including the step of locating a wick in the passage for wicking liquid fragrance from the reservoir to the passage.

18. A method of emitting fragrances, the method comprising the steps of:
providing a fragrance dispenser having first and second sources of fragrance, a dispersing means for dispersing fragrance from the first and second sources of fragrance, and a control means for controlling the dispersing means;
emitting the first fragrance for a first period of time;
emitting no fragrance for a first dwell period following the first period of time;
emitting the second fragrance for a second period of time following the first dwell period of time;
emitting no fragrance for a second dwell period following the second period of time; and
alternatingly emitting the first and second fragrances with dwell periods therebetween by repeating the emitting steps at least once.

19. The method of emitting fragrances of claim 18, further including the step of providing each fragrance with an associated flow path, wherein the control means is also for controlling a size of an outlet of each respective flow path to control the volume of fragrance emitted.

20. The method of emitting fragrances of claim 19, wherein the control means is a shutter.

21. The method of emitting fragrances of claim 19, wherein the control means is a manually operable control member.

22. The method of emitting fragrances of claim 18, wherein the dispersing means includes a fan for generating a flow of air which evaporates the fragrances and disperses the fragrances.

23. The method of emitting fragrances of claim 22, further including the step of controlling power supplied to the fan, thereby controlling a speed of the fan.

24. The method of emitting fragrances of claim 18, further including the step of altering a rate of release of the fragrances by altering the time periods of release.

* * * * *